United States Patent [19]
Yamada et al.

[11] 4,045,454
[45] Aug. 30, 1977

[54] PRODUCTION OF 1-NITROANTHRAQUINONE AND 1-AMINOANTHRAQUINONE

[75] Inventors: Eiji Yamada, Takatsuki; Akira Fukasawa, Toyonaka; Shinzaburo Masaki, Takarazuka, all of Japan

[73] Assignee: Sumitomo Chemical Company, Limited, Osaka, Japan

[21] Appl. No.: 625,475

[22] Filed: Oct. 24, 1975

[30] Foreign Application Priority Data

Oct. 25, 1974 Japan .................................. 49-123714
Apr. 3, 1975 Japan .................................. 50-41009

[51] Int. Cl.$^2$ .................... C07C 79/10; C09B 1/00; C07C 79/36
[52] U.S. Cl. .................................. 260/369; 260/378; 260/379
[58] Field of Search .................. 260/369, 379, 378

[56] References Cited
U.S. PATENT DOCUMENTS 3,959,317  5/1976  Thiem et al. .................... 260/369

Primary Examiner—Paul F. Shaver
Attorney, Agent, or Firm—Birch, Stewart, Kolasch and Birch

[57] ABSTRACT

A process for producing 1-nitroanthraquinone with high purity which comprises treating crude 1-nitroanthraquinone containing as the main impurities dinitroanthraquinones and β-nitroanthraquinone with an alkali sulfite in an aqueous medium under heating and which is characterized in that the crystals of the crude 1-nitroanthraquinone are pulverized by the aid of a pulverizer, a fine pulverizer or an ultra-fine pulverizer prior to and/or during the treatment with the aqueous alkali sulfite; and a process for producing 1-aminoanthraquinone which comprises subjecting the reaction mixture obtained by the said treatment with the alkali sulfite solution mentioned above, if necessary after further fine pulverization, to a reaction with a reducing agent, or ammonia or an aliphatic or aromatic amine.

21 Claims, No Drawings

PRODUCTION OF 1-NITROANTHRAQUINONE AND 1-AMINOANTHRAQUINONE

The present invention relates to processes for producing 1-nitroanthraquinone and 1-aminoanthraquinone with high purity.

Recently, 1-nitroanthraquinone has become considered as a valuable starting material for production of 1-aminoanthraquinone which is an important intermediate for anthraquinone dyestuffs. 1-Aminoanthraquinone has hitherto been produced by sulfonation and amination of anthraquinone. This procedure is disadvantageous in respect of toxicity of the catalysts and apparatus for waste water treatment, and in addition, the reaction rate and the yield are extremely low. According to a method comprising nitration of anthraquinone and subsequent reduction or amination of the product, to the contrary, such drawbacks can be overcome completely.

Crude 1-nitroanthraquinone which is obtained by mononitration of anthraquinone necessarily contains β-nitroanthraquinone, 1,5- and 1,8-dinitroanthraquinones and α,β'-and β, β'-dinitroanthraquinones as by-products.

Among these by-products or unreacted substances, 1,5- and 1,8-(α,α'-)dinitroanthraquinones exert extremely bad influences upon 1-aminoanthraquinone and various dyestuffs derived therefrom. In addition, both of these impurities can be separated off only with great difficulty on purification.

The object of the invention is to provide a method for effectively eliminating these α,α'-dinitroanthraquinones and other by-products such as β-mononitro- and α,β'-dinitroanthraquinones from crude 1-nitroanthraquinone.

Treatment of crude 1-nitroanthraquinone with a sulfite so as to eliminate dinitroanthraquinones and other impurities has already been proposed in U.S. Pat. No. 2,302,729 and in Japanese Pat. Publication No. 29425/1972. It has also been reported in U.S. Pat. No. 2,309,708 that, according to such sulfite treatment, β-nitro derivatives (β- and α, β'-dinitroanthraquinones) can be solubilized and thus eliminated more easily than α,α'-dinitroanthraquinones.

However, these conventional purification methods comprising a sulfite treatment proved, as the result of detailed investigation, to be unsatisfactory, because the effect for elimination of β-nitro- and α,α'-dinitroanthraquinones is restricted to a certain limit beyond which no additional purification effect can be expected, and the thus purified product can not be employed as such as the intermediate for dyestuffs.

In Japanese Patent Publication No. 70954/1974, there has been suggested a method in which the reaction between crude 1-nitroanthraquinone and a sulfite is effected in the presence of a mixture of an inactive organic solvent and water. This method is, however, disadvantageous from the industrial viewpoint, because the reaction must be effected at a temperature higher than the boiling temperature (under normal pressure) of the reaction mixture, which requires expensive apparatus such as a pressure reaction vessel, and in addition, there is necessitated a step for recovery of the organic solvent used which may cause a problem of recovery loss of the solvent. In Japanese Patent Publication No. 129723/1974, there is disclosed another method in which crude 1-nitroanthraquinone is treated with an aqueous solution of a sulfite at a temperature higher than the boiling temperature (under normal pressure) of the reaction mixture. According to this purification method, however, the purity of the obtained 1-nitroanthraquinone is only 93 % or less, as described in the working example in the specification. Such substance can not be employed as an intermediate for production of dyestuffs.

Hitherto, 1-aminoanthraquinone or its derivatives have been industrially produced by condensing anthraquinone-1-sulfonic acid with ammonia or a corresponding amine or by condensing 1-chloroanthraquinone which is derived from anthraquinone-1-sulfonic acid with a corresponding amine. The starting anthraquinone-1-sulfonic acid is prepared by sulfonation of anthraquinone with fuming sulfuric acid. However, this sulfonation reaction requires mercury sulfate as the catalyst, so that there is necessitated complete recovery of mercury discharged in the waste water, which requires enormous expenses. Further, in these reactions, the reaction rate and the yield are low, and besides, the waste water increases extremely the COD and the coloring of rivers into which it is drained.

As the result of extensive studies for developing an industrially advantageous method for purification of crude 1-nitroanthraquinone, it has now been found that highly purified 1-nitroanthraquinone substantially freed from impurities can be obtained in a good yield with an extremely improved selectivity for purification when the treatment of crude 1-nitroanthraquinone with a sulfite is effected under such a condition that crystals of 1-nitroanthraquinone are pulverized by the aid of a pulverizing machine such as a pulverizer, a fine pulverizer or an ultra-fine pulverizer prior to or during the treatment. It has also been found that 1-aminoanthraquinone with high purity can be prepared directly from crude 1-nitroanthraquinone with industrial advantage when the suspension of fine particles of purified 1-nitroanthraquinone obtained by the said sulfite treatment, by which the impurities such as α,β'-dinitroanthraquinones, β-mononitroanthraquinone and α,β'-dinitroanthraquinones can be efficiently solubilized, is subjected to amination or reduction without isolation of the product.

According to the invention, there is provided a process for producing 1-nitroanthraquinone with high purity which comprises treating crude 1-nitroanthraquinone containing as the main impurities dinitroanthraquinones and β-nitroanthraquinone with an alkali sulfite in an aqueous medium under heating, and which is characterized in that the crystals of the crude 1-nitroanthraquinone are pulverized prior to and/or during the treatment with the aqueous alkali sulfite and a process for producing 1-aminoanthraquinone which comprises subjecting the reaction mixture obtained by the said treatment with the alkali sulfite solution mentioned above, if necessary after further fine pulverization, to a reaction with a reducing agent, or ammonia or an aliphatic or aromatic amine.

As the crude 1-nitroanthraquinone of the invention, there is preferably employed the one which is obtained, for instance, according to the method described in Japanese Patent Publication No. 5430/1974, by nitrating anthraquinone until the proportion of the unreacted starting material becomes 1 % or less, diluting the reaction mixture to make the nitric acid concentration around 90 %, removing off the dinitroanthraquinones which are rich in 1,5-compounds by filtration and collecting all of the nitro compounds contained in the filtrate. There may be also employed the crude 1-nitroanthraquinone which is obtained by the mixed acid method, e.g. by mononitrating with a theoretical amount of nitric acid in the presence of 90 % $H_2SO_4$, followed by collection of all of the reaction product.

In the purification method according to the invention, the crude 1-nitroanthraquinone is pulverized by the aid of a pulverizing machine prior to or during the treatment. As the pulverizing machine, there may be exemplified a pulverizer (e.g. crusher, hammer mill), a fine pulverizer (e.g. ball mill, tube mill, rod mill, kneader, roller mill) and an ultra-fine pulverizer (e.g. jet mill, micronizer, colloid mill, sand mill using fine particles of stone or glass, ultrasonic wave-oscillator). Among them, an ultra-fine pulverizer of the wet type is preferable. By the use of such a pulverizer, crystals of crude 1-nitroanthraquinone being usually from several tens to several hundred microns in particle size are pulverized into fine particles of 10 $\mu$ or less, preferably 5 – 0.01 $\mu$, in particle size. It is desired to incorporate into the pulverization system a small amount of an anionic surface active agent and/or a nonionic surface active agent, since the addition of such substances contributes not only to the stabilization of the fine particles but also to improvement of the selectivity in the reaction of the crude 1-nitroanthraquinone pulverized with an aqueous solution of a sulfite.

As the alkali sulfite to be used in the invention, there are employed sulfites and bisulfites of lithium, sodium, potassium and ammonium. The amount of such sulfite to be used is determined depending on the amount of impurities contained in the crude 1-nitroanthraquinone. In usual, 0.1 to 5 parts by weight of the alkali sulfite is used to 1 part by weight of the crude 1-nitroanthraquinone. The concentration of the aqueous sulfite solution is usually about 0.5 to 20 % by weight, preferably 1 to 15 % by weight.

As the nonionic surface active agent to be used in the invention, there may be exemplified higher alcohol-ethylene oxide adducts, alkylphenol-ethylene oxide adducts, fatty acid-ethylene oxide adducts, fatty acid ester of polyalcohol-ethylene oxide adducts, higher alkylamine-ethylene oxide adducts, fatty acid amine-ethylene oxide adducts, fat-ethylene oxide adducts, polypropylene glycol-ethylene oxide adducts, fatty acid esters of glycerol, fatty acid esters of pentaerythritol, fatty acid esters of sorbitol and sorbitan, fatty acid esters of sorbitol and sorbitan-ethylene oxide adducts, fatty acid esters of sugar, alkyl ethers of polyalcohols, fatty acid amines of alkanolamine, etc. Specific examples are polyoxyethylene lauryl ether, polyoxyethylene oleyl ether, polyoxyethylene octylphenol ether, polyoxyethylene nonylphenol ether, sorbitan monolaurate, sorbitan distearate, polyoxyethylene sorbitan monolaurate, polyethylene glycol monostearate, polyethylene glycol distearate, glycerin monostearate, etc.

As the anionic surface active agent to be used in the invention, there may be exemplified fatty acid salts, salts of sulfuric esters of higher alcohols, salts of sulfuric esters of higher alkylethers, salts of sulfuric esters of liquid fatty oils, sulfates of aliphatic amines and aliphatic amides, sulfonated olefins, salts of alkylaryl sulfonic acids, salts of paraffinsulfonic acid, salts of fatty acid amide sulfonic acid, sulfonates of dibasic fatty acid esters, salts of lignin sulfonic acid, salts of naphthalene sulfonic acid condensed with formalin, salts of phosphoric acid esters of higher alcohols, salts of polyoxyethylene sulfate, etc. Specific examples are sodium oleate, potassium salts of fatty acids, sodium salts of laurin sulfuric ester, sodium alkylnaphthalenesulfonate, sodium dialkyl sulfosuccinate, polyoxyethylene alkylphenyl sulfate sodium salts, salts of alkyl phosphates, the formalin-condensation product of Schaffer's acid and cresol, etc.

Among the said nonionic surface active agents, those being 5 to 20, preferably 7 to 20, in HLB are particularly effective for the purification method of the invention, since they exhibit a high selectivity on the water-solubilization of dinitroanthraquinones and $\beta$-nitroanthraquinone in the treatment with the aqueous sulfite solution. By the excellent action of such surface active agents, the greater part of the dinitroanthraquinones and $\beta$-nitroanthraquinone contained in the crude 1-nitroanthraquinone can be water-solubilized and thus eliminated, and 95 % of the 1-nitroanthraquinone in the crude 1-nitroanthraquinone can be isolated as a purified product with a purity exceeding 98 %.

The amount of the surface active agent to be used is 0.001 to 5 parts by weight, preferably 0.05 to 1 part by weight, to 10 parts by weight of the crude 1-nitroanthraquinone.

In the reaction according to the present method, there exists a relationship with an inverse proportion between the reaction temperature and the reaction time. In the usual case, it is industrially advantageous to effect the reaction at a temperature of about 50° to 150° C, preferably about 80 to 120° C, for about 1 to 24 hours under normal pressure or an elevated pressure of 0.5 to 5 kg/cm². The optimal reaction temperature and time are varied according to the amount of the impurities and other reaction conditions determined depending thereupon.

According to the method of the invention, there can be obtained a highly purified 1-nitroanthraquinone which does not contain impurities other than a trace amount of unreacted anthraquinone. The thus purified 1-nitroanthraquinone may be isolated from the reaction mixture or taken as such in the reaction mixture form after the alkali sulfite treatment, and subjected to a conventional reduction or amination procedure to obtain 1-aminoanthraquinone.

For isolation of the purified 1-nitroanthraquinone, a specific isolation method is required, since, in the reaction mixture after the alkali sulfite treatment, the purified 1-nitroanthraquinone is present in fine particle form. For example, a filter paper with extremely fine texture is employed, or the reaction mixture is subjected to centrifugation and the supernatant is removed off by decantation.

There may be also employed a high polymer coagulant for catching fine particles. As such a coagulant, a cationic one such as polyacrylamide is used. Further, the isolation may be effected by adding to the reaction mixture after the alkali sulfite treatment an inorganic salt such as sodium chloride so as to promote the growth of crystals of purified 1-nitroanthraquinone and collecting the crystals by filtration.

Furthermore, the reaction mixture may be kept at a high temperature for several hours together with an inactive organic solvent so as to make the crystals of purified 1-nitroanthraquinone grow to obtain a sufficient particle size for isolation by filtration. In this case, the filtration is effected after recovery of the inactive organic solvent. As the solvent to be used in this method, a water-insoluble one is desirable when considering its recovery. Specific examples of such solvent are benzene, toluene, o-, m- or p-xylene, ethylbenzene, monochlorobenzene, o-, m- or p-dichlorobenzene, 1,3,5-trichlorobenzene, nitrobenzene, o-nitrotoluene, etc. The amount of the solvent to be used is usually 0.1 to 3 times, preferably 0.3 to 1.5 times as large as the amount of the purified 1-nitroanthraquinone. The treatment with the solvent is usually effected for 1 to 10 hours.

In any of these isolation methods, the yield of 1-nitroanthraquinone is not influenced by such isolation operations, and an appropriate method can be selected depending on the case.

The purified 1-nitroanthraquinone thus obtained by the treatment of the crude 1-nitroanthraquinone in fine particle form with a sulfite may be, directly without being isolated from the reaction mixture, subjected to a reaction with ammonia or an aliphatic or aromatic amine in an amount of 1 to 20 molar ratio at 50° to 170° C for several hours in an autoclave, or to a conventional reduction in the presence of a reducing agent such as sodium sulfide, sodium hydrosulfide or glucose under an alkaline condition or in the presence of a reducing agent such as zinc, iron or tin under an acidic condition, or to hydrogenation in the presence of a catalyst such as Raney nickel or palladium-carbon under normal or elevated pressure of hydrogen at 50° to 160° C for about 3 to 15 hours, so as to obtain the objective aminoanthraquinone derivatives.

A further pulverizing operation may be effected prior to or during the amination or the reduction.

As the aliphatic and aromatic amine to be used in the invention, there may be exemplified methylamine, ethylamine, propylamine, butylamine, hexylamine, ethanolamine, methoxypropylamine, ethoxypropylamine, dimethylaminopropylamine, dimethylamine, diethylamine, cyclohexylamine, benzylamine, phenethylamine, aniline, N-methylaniline, p-chloroaniline, orthotoluidine, metatoluidine, paratoluidine, paranisidine, paraphenetidine, metaxylidine, mesidine, etc.

The thus obtained 1-aminoanthraquinone derivative has a high purity and does not contain impurities other than a trace amount of unreacted anthraquinone.

According to the method of the invention, effective purification of crude 1-nitroanthraquinone can be attained substantially in one step, and the thus purified product can be subjected to amination or reduction directly without being isolated from the reaction mixture, so that the operations are easy, and the amount of the waste water is greatly reduced. In addition, a much higher yield can be attained in comparison with the conventional sulfonation method. Thus, the method of the invention has great advantages in respect of the yield, the cost, the operation and the prevention of environmental pollution.

The 1-aminoanthraquinone derivative obtained according to the method of the invention can be advantageously employed as an intermediate for production of dyestuffs to afford excellent products comparable to those with a good color which are prepared from 1-aminoanthraquinone derivatives obtained by the conventional sulfonation method.

Practical and presently preferred embodiments of the invention are illustratively shown in the following examples in which parts and percents are by weight.

EXAMPLE 1

A mixture of crude 1-nitroanthraquinone (10 parts) containing 0.3 % of anthraquinone, 12 % of α,α'-dinitroanthraquinones and 5 % of 2-nitroanthraquinone, which is obtained by preliminary purification with nitric acid, water (50 parts), naphthalenesulfonic acid-formalin condensation product (1 part) and glass beads being about 1 mm in particle size (60 parts), is stirred vigorously at room temperature for about 5 hours. Sodium sulfite (3 parts) is added thereto, and the temperature is elevated up to 98° C. The mixture is kept at the same temperature for several hours under vigorous stirring. When dinitroanthraquinones are not detected any more by sampling of the reaction mixture, the glass beads are removed off by filtration through a wire net of 60 mesh. The collected glass beads are washed, and the washing is combined with the filtrate. From the resultant filtrate mixture, a slurry of 1-nitroanthraquinone is isolated by a centrifugal precipitation procedure. It is washed with water several times and then dried.

Thus, there is obtained 1-nitroanthraquinone with high purity containing neither dinitroanthraquinones nor β-nitroanthraquinone. Yield, 95 %. The thus obtained 1-nitroanthraquinone can be reduced into 1-aminoanthraquinone which is utilizable as an intermediate for production of dyestuffs.

EXAMPLE 2

A mixture of crude 1-nitroanthraquinone (10 parts) containing 73.0 % of 1-nitroanthraquinone, 0.4 % of anthraquinone, 13.3 % of α,α'-dinitroanthraquinones and 4.4 % of 2-nitroanthraquinone, which is obtained by preliminary purification with nitric acid, water (25 parts), polyoxyethylene octylphenol ether (HLB, 13.1) (1 part) and glass beads being about 1 mm in particle size (70 parts), is stirred vigorously at room temperature for about 2 hours. Then, the mixture is filtered through a wire net of 100 mesh. The collected glass beads are washed, and the washing is combined with the filtrate. To the resultant filtrate mixture in slurry form, sodium sulfite (3.5 parts) is added, and the temperature is elevated up to 100° C. The mixture is kept at the same temperature for about 6 hours under vigorous stirring. After the completion of the reaction, monochlorobenzene (2.5 parts) is added, and the mixture is kept at refluxing temperature for 2 hours. Then, monochlorobenzene is eliminated, and purified 1-nitroanthraquinone is isolated from the mother liquor, washed with water several times and dried.

Thus, there is obtained purified 1-nitroanthraquinone (7.1 parts) containing 98.2 % of 1-nitroanthraquinone, 0.6 % of α,α'-dinitroanthraquinones and 0.8 % of anthraquinone. The yield of purified 1-nitroanthraquinone is 95.5 %.

EXAMPLE 3

A mixture of crude 1-nitroanthraquinone (10 parts) having the same composition as in Example 2, water (25 parts), polyoxyethylene nonylphenol ether (HLB, 18.9) (1 part) and glass beads being about 1 mm in particle size (70 parts) is stirred vigorously at room temperature for about 2 hours. Then, the mixture is filtered through a wire net of 100 mesh. The collected glass beads are washed, and the washing is combined with the filtrate. To the resultant filtrate mixture in slurry form, sodium sulfite (3.5 parts) is added, and the temperature is elevated up to 100° C. The mixture is kept at the same temperature for about 6 hours under vigorous stirring. After completion of the reaction, sodium chloride (3 parts) is added, and the mixture is kept at 100° C for about 4 hours. Then, purified 1-nitroanthraquinone is isolated from the mother liquor, washed with water several times and then dried.

Thus, there is obtained purified 1-nitroanthraquinone (6.9 parts) containing 98.0 % of 1-nitroanthraquinone, 0.7 % of α,α'-dinitroanthraquinones and 0.8 % of anthraquinone.

EXAMPLE 4

A mixture of crude 1-nitroanthraquinone having the same composition as in Example 2 (10 parts), water (25 parts), polyoxyethylene nonylphenyl ether (0.5 parts), a naphthalenesulfonate-formalin condensation product (0.5 part) and glass beads being about 1 mm in particle size (70 parts) is stirred vigorously at room temperature for about 2 hours. Then, the mixture is filtered through a wire net of 100 mesh. The collected glass beads are washed, and the washing is combined with the filtrate. To the resultant filtrate mixture in slurry form, sodium sulfite (3.5 parts) is added, and the temperature is elevated up to 100° C. The mixture is kept at the same temperature for about 6 hours under vigorous stirring. After the reaction, a high polymer coagulant (dimethylaminomethacrylate-acrylamide copolymer; average molecular weight, 5 million) is added in a concentration of 400 ppm to the reaction mixture, and the mixture is stirred at room temperature for about 4 hours. Then, the mixture is filtered, and the purified 1-nitroanthraquinone isolated from the mother liquor is washed with water several times and dried.

The thus obtained 1-nitroanthraquinone (7.2 parts) contains 96.2 % of 1-nitroanthraquinone and 1.3 % of α,α'-dinitroanthraquinones.

EXAMPLE 5

A mixture of crude 1-nitroanthraquinone having the same composition as in Example 2 (10 parts), water (25 parts), polyoxyethylene sorbitan monolaurate (1 part) and pulverized balls (SUS) being about 3 mm in particle size (200 parts) is stirred vigorously at room temperature for about 2 hours. Then, the mixture is filtered through a wire net of 60 mesh. The pulverized balls collected are washed, and the washing is combined with the filtrate. To the resultant filtrate mixture, sodium sulfite (3.5 parts) is added, and the temperature is elevated up to 100° C. The mixture is kept at the same temperature for about 6 hours under vigorous stirring. After completion of the reaction, toluene (5.0 parts) is added, and the mixture is kept at refluxing temperature for 2 hours. Then, toluene is eliminated, and purified 1-nitroanthraquinone is isolated from the mother liquor, washed with water several times and dried.

Thus, there is obtained purified 1-nitroanthraquinone (7.0 parts) containing 98.6 % of 1-nitroanthraquinone, 0.6 % of dinitroanthraquinones and 0.8 % of anthraquinone.

EXAMPLE 6

In a 750 part-volume stainless steel beaker, there are charged crude 1-nitroanthraquinone having the same composition as in Example 2 (80 parts), water (200 parts), polyethylene glycol monostearate (0.8 part), sodium sulfite (24 parts) and pulverized balls (SUS) being about 3 mm in particle size (1600 parts), and the mixture is stirred at 90° C for 8 hours and then at 97° C for 6 hours under a rotation speed of 400 rpm. After completion of the reaction, the reaction mixture is cooled and filtered. The pulverized balls collected are washed with warm water (200 parts), and the washing is combined with the filtrate containing fine crystals of purified 1-nitroanthraquinone. To the resultant suspension (503 parts), xylene (20 parts) is added, and the mixture is kept at refluxing temperature for 6 hours. Then, xylene is eliminated, and purified 1-nitroanthraquinone is isolated from the mother liquor, washed with water several times and dried.

Thus, there is obtained purified 1-nitroanthraquinone (57.3 parts) containing 98.0 % of 1-nitroanthraquinone, 0.7 % of dinitroanthraquinones and 1.0 % of anthraquinone.

EXAMPLE 7

To a suspension (about 60 parts) which is obtained by treatment of crude 1-nitroanthraquinone (A) (10 parts) with sodium sulfite as in Example 2, sodium sulfide flakes (purity, 60 %) (9.4 parts) are added, and the mixture is stirred at 45° C for 3 hours and then at 95° C for 2 hours whereby reduction proceeds almost quantitatively. After cooling, the reaction mixture is filtered, and the product is washed and dried to obtain 1-aminoanthraquinone with a high purity of 98 % (6.3 parts). The yield with respect to 1-nitroanthraquinone in the starting material is 95 %. (The detailed composition is as shown in Table 1. The yield is calculated in terms of the molecular weight.)

EXAMPLE 8

A mixture of a wet cake of crude 1-nitroanthraquinone (A) (solid content, 28.6 %) (35 parts) and a naphthalenesulfonic acid salt-formalin condensation product (1 part) is finely pulverized by the aid of a wet type pulverizer using stainless steel balls (3 mmφ). The resultant finely pulverized wet cake (36 parts) is charged into a reaction vessel, a 10.8 % aqueous solution of sodium sulfite (28 parts) is added thereto, and the mixture is stirred at 100° C for 9 hours. After the mixture is cooled to 45° C, sodium sulfide flakes (purity, 60 %) (9.4 parts) are added, and the mixture is treated in the same manner as in Example 7 to obtain 1-aminoanthraquinone with high purity (6.3 parts). The composition is as shown in Table 1.

EXAMPLE 9

To a suspension (503 parts) containing fine crystals of purified 1-nitroanthraquinone, which is obtained by treatment of crude 1-nitroanthraquinone (B) (80 parts) as in Example 6, sodium sulfide flakes (purity, 60 %) (75.2 parts) are added, and the mixture is treated as in Example 7 to obtain 1-aminoanthraquinone with high purity (50.8 parts). The yield and the composition are as shown in Table 1.

EXAMPLE 10

Crude 1-nitroanthraquinone (A) (10 parts) is treated with sodium sulfite in the same manner as in Example 2. The resultant suspension is subjected to centrifugation, and the supernatant is removed off by decantation. The residual wet cake comprising fine particles of 1-nitroanthraquinone with high purity is charged into an autoclave together with water (21 parts) and kept at 125° C for 14 hours while introducing gaseous ammonia (7 parts) therein. When the completion of the amination is confirmed, ammonia is recovered, and the reaction mixture is cooled and filtered. The collected product is washed and dried to obtain 1-aminoanthraquinone with high purity (6.2 parts). The composition and the yield are as shown in Table 1.

EXAMPLE 11

In an autoclave, there are charged a wet cake of finely pulverized crude 1-nitroanthraquinone (A) containing a small amount of a surface active agent, which is obtained as in Example 2 (solid content, 28.6 %) (70 parts), sodium sulfite (5 parts), water (50 parts) and liquid ammonia (20 parts), and the contents are stirred at 100° C for 6 hours and then 135° C for 12 hours. The reaction mixture is then at treated as in Example 10 to obtain crude 1-aminoanthraquinone, which is purified with an organic solvent by a conventional procedure so as to eliminate a trace amount of impurities with a violet color to give 1-aminoanthraquinone with high purity (12 parts). The composition is as shown in Table 1.

Table 1

| | | | Yield (%) | Composition (weight %) | | | | |
|---|---|---|---|---|---|---|---|---|
| | | | | I | II | III | IV | V |
| Starting material (nitro compound) | (A) | | | 0.4 | 4 | 73 | 1 | 12 |
| | (B) | | | 1 | 5 | 74 | 2 | 8 |
| Product (amino compound) | Example No. | 7 | 95 | 0.6 | 0 | 98 | 0.4 | 0.4 |
| | | 8 | 94 | 0.8 | 0 | 96 | 0.5 | 0.8 |
| | | 9 | 94 | 1.5 | 0 | 97 | 0.4 | 0.4 |
| | | 10 | 92 | 0.7 | 0 | 96 | 0.2 | 0.1 |
| | | 11 | 92 | 0.6 | 0 | 99 | 0.1 | 0.1 |

Note:
Yield: yield of 1-aminoanthraquinone in the product to 1-nitroanthraquinone in the starting material.
I anthraquinone
II 2-nitro(or amino)anthraquinone
III 1-nitro(or amino)anthraquinone
IV 1,5-dinitro(or diamino)anthraquinone
V 1,8-dinitro(or diamino)anthraquinone

EXAMPLE 12

To a filtrate mixture containing purified 1-nitroanthraquinone finely pulverized (25.3 parts), which is obtained as in Example 1, a 30 % aqueous solution of methylamine (60 parts) and sodium carbonate (10 parts) are added, and the mixture is heated at 100° C for 5 to 10 hours in an autoclave. After completion of the reaction, the crystals formed are collected by filtration, washed and then dried to obtain 1-methylaminoanthraquinone (23.2 parts) as a substance with a clear red color. Yield, 98 %. M.P. 172° C. This compound is useful as a coloring agent for resins which shows a good dispersibility and can afford an excellent color.

EXAMPLE 13

A filtrate mixture containing purified 1-nitroanthraquinone (purity, 98 %) (25.3 parts), which is obtained as in Example 12, is further subjected to fine pulverization. Cyclohexylamine (30 parts) (molar ratio, about 3.0) and sodium carbonate (5 parts) are added thereto, and the mixture is heated at 95° to 98° C under refluxing. After completion of the reaction, excess cyclohexylamine is removed off by azeotropic distillation together with water to recover a 40 % aqueous solution of cyclohexylamine, which can be reutilized. The residual reaction mass is filtered to collect crystals, which are washed and dried to obtain N-cyclohexyl-1-aminoanthraquinone (28.2 parts) as a substance with a red color. Yield, 97 %. M.P. 145° C.

EXAMPLE 14

In an autoclave, there are charged a filtrate mixture containing purified 1-nitroanthraquinone finely pulverized (25.3 parts), which is obtained as in Example 2, and palladium-carbon (palladium, 10 %) (2.5 parts), and hydrogenation is effected at 130 to 140° C under a hydrogen pressure of 20 - 10 kg/cm$^2$. After 8 hours, consumption of the theoretical amount of hydrogen is confirmed. The reaction mixture is taken out from the autoclave and filtered. The resultant cake is washed, and the catalyst is removed therefrom to obtain 1-aminoanthraquinone (20.1 parts).

What is claimed is:

1. In a process for producing 1-nitroanthraquinone with high purity by treating crude 1-nitroanthraquinone containing as the main impurities dinitroanthraquinones and β-nitroanthraquinones with an aqueous alkali sulfite or bisulfite solution under heating, the improvement which comprises pulverizing the crude 1-nitroanthraquinone prior to and/or during the treatment with the aqueous alkali sulfite or bisulfite solution.

2. The process according to claim 1, wherein the particles of the pulverized crude 1-nitroanthraquinone are 10 μ or less in particle size.

3. The process according to claim 1, wherein the alkali sulfite is a member selected from the group consisting of the sulfites of lithium, sodium, potassium and ammonium.

4. The process according to claim 1, wherein the alkali bisulfite is a member selected from the group consisting of the bisulfites of lithium, sodium, potassium and ammonium.

5. The process according to claim 1, wherein the amount of the alkali sulfite or bisulfite employed is 0.1 to 5 parts by weight to 1 part by weight of the crude 1-nitroanthraquinone.

6. The process according to claim 1, wherein the concentration of the alkali sulfite or bisulfite in the aqueous alkali sulfite or bisulfite solution employed is 0.5 to 20% by weight.

7. The process according to claim 1, wherein the pulverization is effected in the presence of an anionic surface active agent and/or a nonionic surface active agent.

8. The process according to claim 7, wherein the nonionic surface active agent is a member selected from the group consisting of higher alcohol-ethylene oxide adducts, alkylphenol-ethylene oxide adducts, fatty acid-ethylene oxide adducts, fatty acid esters of polyalcohol-ethylene oxide adducts, higher alkylamine-ethylene oxide adducts, fatty acid amide-ethylene oxide adducts, fat-ethylene oxide adducts, polypropylene glycol-ethylene oxide adducts, fatty acid esters of glycerol, fatty acid esters of pentaerythritol, fatty acid esters of sorbitol and sorbitan, fatty acid esters of sorbitol and sorbitan-ethylene oxide adducts, fatty acid esters of sugar, alkyl ethers of polyalcohols and fatty acid amides of alkanolamine.

9. The process according to claim 7, wherein the nonionic surface active agent is a member selected from the group consisting of polyoxyethylene lauryl ether, polyoxyethylene oleyl ether, polyoxyethylene octylphenol ether, polyoxyethylene nonylphenol ether, sorbitan monolaurate, sorbitan distearate, polyoxyethylene sorbitan monolaurate, polyethylene glycol monostearate, polyethylene glycol distearate and glycerin monostearate.

10. The process according to claim 7, wherein the anionic surface active agent is a member selected from the group consisting of fatty acid salts, salts of sulfuric esters of higher alcohols, salts of sulfuric esters of higher alkylethers, salts of sulfuric esters of liquid fatty oils, sulfates or aliphatic amines and aliphatic amides, sulfonated olefins, salts of alkylaryl sulfonic acids, salts of paraffinsulfonic acids, salts of fatty acid amide sulfonic acids, sulfonates of dibasic fatty acid esters, salts of lignin sulfonic acid, salts of naphthalene sulfonic acid condensed with formalin, salts of phosphoric acid esters of higher alcohols and salts of polyoxyethylene sulfate.

11. The process according to claim 7, wherein the anionic surface active agent is a member selected from the group consisting of sodium oleate, potassium salts of fatty acids, sodium salts of laurin sulfuric ester, sodium alkylnaphthalenesulfonate, sodium dialkyl sulfosuccinate, polyoxyethylene alkylphenyl sulfate sodium salts, salts of alkyl phosphates and formalin-condensation products of Schaffer's acid and cresol.

12. The process according to claim 7, wherein the amount of the surface active agent employed is 0.001 to 5 parts by weight to 10 parts by weight of the crude 1-nitroanthraquinone.

13. The process according to claim 1, wherein the treatment with the alkali sulfite is effected at a temperature of about 50° to 150° C. under normal or elevated pressure.

14. The process according to claim 1, wherein the treatment with the alkali sulfite is effected for a duration of about 1 to 24 hours.

15. In a process for producing 1-aminoanthraquinone by treating crude 1-nitroanthraquinone containing as the main impurities dinitroanthraquinones and β-nitroanthraquinone with an aqueous alkali sulfite or bisulfite solution and then reacting the resulting mixture or the purified 1-nitroanthraquinone isolated from the resulting mixture with a reducing agent, or ammonia or an aliphatic or aromatic amine, the improvement which comprises pulverizing the crude 1-nitroanthraquinone prior to and/or during the treatment with the aqueous alkali sulfite or bisulfite solution.

16. The process according to claim 15, wherein the resulting mixture or the purified 1-nitroanthraquinone isolated from the resulting mixture is further pulverized prior to and/or during the reaction with the reducing agent, or ammonia or the aliphatic or aromatic amine.

17. The process according to claim 15, wherein the aliphatic or aromatic amine is a member selected from the group consisting of methylamine, ethylamine, propylamine, butylamine, hexylamine, ethanolamine, methoxypropylamine, ethoxypropylamine, dimethylaminopropylamine, dimethylamine, diethylamine, cyclohexylamine, benzylamine, phenethylamine, aniline, N-methylaniline, p-chloroaniline, orthotoluidine, metatoluidine, paratoluidine, paraanisidine, paraphenetidine, metaxylidiene and mesidine.

18. The process according to claim 15, wherein the reducing agent is sodium sulfide, sodium hydrosulfide or glucose.

19. The process according to claim 15, wherein ammonia or the aliphatic or aromatic amine is used in an amount of 1 to 20 molar ratio.

20. The process according to claim 19, wherein the reaction is effected at 50° to 170° C. under an elevated pressure.

21. The process according to claim 15, wherein the reaction is effected by hydrogenation in the presence of palladium-carbon or Raney nickel as the catalyst.

* * * * *